United States Patent
Fang et al.

(10) Patent No.: US 10,683,548 B2
(45) Date of Patent: Jun. 16, 2020

(54) **SINGLE NUCLEOTIDE POLYMORPHISM IN HLA-B*15:02 AND USE THEREOF**

(71) Applicant: Millennium Health, LLC, San Diego, CA (US)

(72) Inventors: Hua Fang, San Diego, CA (US); Xiequn Xu, San Diego, CA (US); Tanya Moreno, San Diego, CA (US); Matthew Dedek, San Diego, CA (US); Kulvi Kaur, Encinitas, CA (US)

(73) Assignee: Millennium Health, LLC, San Diego, CA (US)

( * ) Notice: Subject to any disclaimer, the term of this patent is extended or adjusted under 35 U.S.C. 154(b) by 153 days.

(21) Appl. No.: 15/933,325

(22) Filed: Mar. 22, 2018

(65) Prior Publication Data

US 2018/0216190 A1 Aug. 2, 2018

Related U.S. Application Data

(62) Division of application No. 15/195,114, filed on Jun. 28, 2016, now Pat. No. 9,932,638.

(60) Provisional application No. 62/186,219, filed on Jun. 29, 2015.

(51) Int. Cl.
*C12Q 1/68* (2018.01)
*A61K 31/55* (2006.01)
*C12Q 1/6883* (2018.01)

(52) U.S. Cl.
CPC ............ *C12Q 1/6883* (2013.01); *A61K 31/55* (2013.01); *C12Q 2600/106* (2013.01); *C12Q 2600/156* (2013.01)

(58) Field of Classification Search
CPC ............ C12Q 1/6883; C12Q 2600/106; C12Q 2600/156
See application file for complete search history.

(56) References Cited

U.S. PATENT DOCUMENTS 9,932,638 B2 4/2018 Fang et al.
2012/0329045 A1 12/2012 Chung et al.
2014/0274764 A1 9/2014 Zhu et al.

OTHER PUBLICATIONS

Liu, X et al., "Tag SNPs for HLA-B Alleles that are Associated with Drug Response and Disease Risk in the Chinese Han Population", Pharmacogenomics Journal, vol. 15, No. 5, pp. 467-472, (Mar. 10, 2015).
He, Yijing et al., "Accusracy of SNPs to Predict Risk of HLA Alleles Associated with Drug-Induced Hypersensitivity Events Across Racial Groups", Pharmacogenomics, vol. 16, No. 8, pp. 817-824, (Jun. 17, 2015).
https://www.snpedia.com/index.php?title=Rs144012689&oldid=488929 [retrieved on Jul. 31, 2012].
Supplementary European Search Report for corresponding European Application No. 16818674, dated Oct. 30, 2018.
Chen et al., Carbamazepine-Induced Toxic Effects and HLA-B*1502 Screening in Taiwan, New England Journal of Medicine, 364:1126-33, Mar. 24, 2011.
Ferrell Jr. et al., Carbamazepine, HLA-B*1502 and Risk of Stevens-Johnson syndrome and toxic epidermal necrolysis: US FDA recommendations, Pharmacogenomics. Oct. 2008; 9(10): 1543-1546.
Pillai, et al., "Predicting HLA alleles from high-resolution SNP data in three Southeast Asian populations", Human Molecular Genetics, pp. 1-21, Apr. 3, 2014.
PCT International Search Report and Written Opinion issued in International Application No. PCT/US2016/040075 dated Oct. 31, 2016.

*Primary Examiner* — David C Thomas
(74) *Attorney, Agent, or Firm* — Greenberg Traurig, LLP; Fang Xie

(57) ABSTRACT

Disclosed herein is a novel single nucleotide polymorphism (SNP) in HLA-B*15:02 that can be used as a biomarker for carbamazepine-induced severe adverse skin reactions in Asians. Also provided herein are methods and reagents for assessing the specific SNP, and applying the SNP in predicting an increased risk of carbamazepine-induced severe adverse skin reactions.

21 Claims, 1 Drawing Sheet

Specification includes a Sequence Listing.

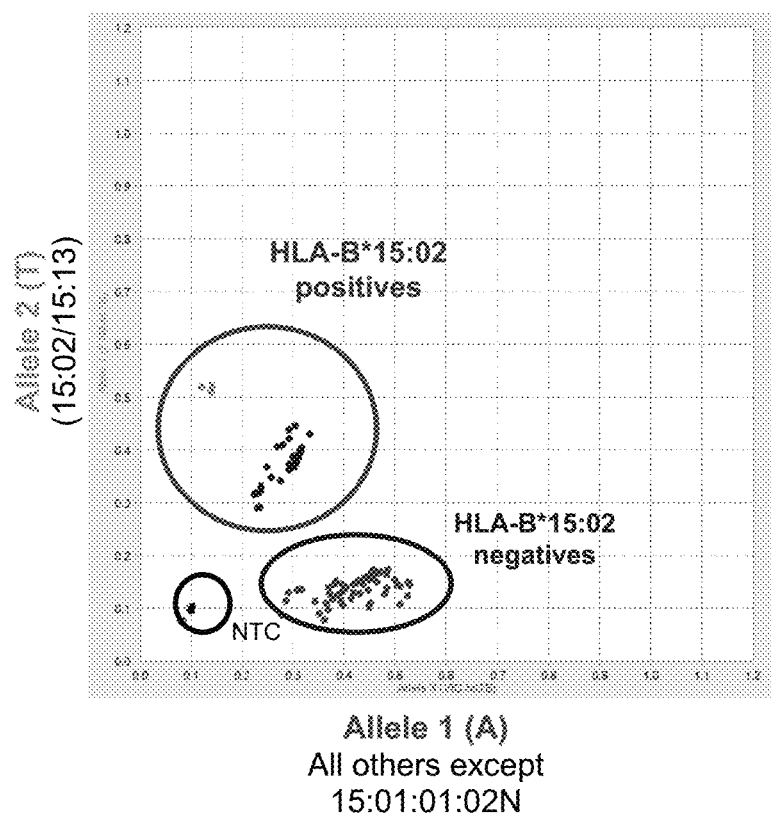

SEQUENCE LISTING

```
<160> NUMBER OF SEQ ID NOS: 10

<210> SEQ ID NO 1
<211> LENGTH: 22
<212> TYPE: DNA
<213> ORGANISM: Homo sapiens

<400> SEQUENCE: 1
tcaagcccca ggtagaagtg tt                                            22

<210> SEQ ID NO 2
<211> LENGTH: 22
<212> TYPE: DNA
<213> ORGANISM: Homo sapiens

<400> SEQUENCE: 2
cattgtcaca tgtgctgcac aa                                            22

<210> SEQ ID NO 3
<211> LENGTH: 20
<212> TYPE: DNA
```

```
<213> ORGANISM: Homo sapiens

<400> SEQUENCE: 3
agtgttccct gcctcattac                                              20

<210> SEQ ID NO 4
<211> LENGTH: 20
<212> TYPE: DNA
<213> ORGANISM: Homo sapiens

<400> SEQUENCE: 4
agagtaagtg ctggcacaca                                              20

<210> SEQ ID NO 5
<211> LENGTH: 17
<212> TYPE: DNA
<213> ORGANISM: Homo sapiens

<400> SEQUENCE: 5
aagcagcatc ctcacag                                                 17

<210> SEQ ID NO 6
<211> LENGTH: 17
<212> TYPE: DNA
<213> ORGANISM: Homo sapiens

<400> SEQUENCE: 6
aagcagcatc cacacag                                                 17

<210> SEQ ID NO 7
<211> LENGTH: 17
<212> TYPE: DNA
<213> ORGANISM: Homo sapiens

<400> SEQUENCE: 7
aagcagcatg cacacag                                                 17

<210> SEQ ID NO 8
<211> LENGTH: 21
<212> TYPE: DNA
<213> ORGANISM: Homo sapiens

<400> SEQUENCE: 8
cagcatcctc acaggggcta a                                            21

<210> SEQ ID NO 9
<211> LENGTH: 21
<212> TYPE: DNA
<213> ORGANISM: Homo sapiens

<400> SEQUENCE: 9
cagcatccac acaggggcta a                                            21

<210> SEQ ID NO 10
<211> LENGTH: 21
<212> TYPE: DNA
<213> ORGANISM: Homo sapiens

<400> SEQUENCE: 10
cagcatgcac acaggggcta a                                            21
```

SINGLE NUCLEOTIDE POLYMORPHISM IN HLA-B*15:02 AND USE THEREOF

CROSS-REFERENCE TO RELATED APPLICATIONS

This application is a divisional of U.S. patent application Ser. No. 15/195,114 filed Jun. 28, 2016, which claims priority to and the benefit of U.S. Provisional Application No. 62/186,219 filed Jun. 29, 2015, the entire disclosure of which is incorporated herein by reference.

FIELD

The present disclosure is directed to methods and compositions for HIA-B*15:02 genotyping, in particular single nucleotide polymorphisms (SNPs) therein and use thereof. The SNP can serve as a biomarker for carbamazepine (and its related drugs) induced severe adverse skin reactions.

BACKGROUND

Carbamazepine (CBZ) is a drug that is frequently prescribed in treatment of epilepsy and bipolar disorder. HLA-B*15:02 is strongly associated with carbamazepine-induced life-threatening inflammatory adverse reactions in skin and mucous membrane (Chung et al., *Medical genetics: a marker for Stevens-Johnson syndrome*, Nature, 2004, 428 (6982): p. 486; Chen et al., *Carbamazepine-induced toxic effects and HLA-B*15:02 screening in Taiwan*, N Engl J Med, 2011, 364(12): pp. 1126-33). See also www.fda.gov/Drugs/DrugSafety/PostmarketDrugSafetyInformationforPatientsandProviders/ucm 124718.htm. Thus, HLA-B*15:02 screening is warranted in patients requiring carbamazepine therapy (*Tegretol® and Tegretol-XR prescribing information: FDA approved labeling*. 2014). Currently, the detection of HLA-B*15:02 through HLA typing is feasible but technically challenging due to the highly polymorphic and homologous nature of all HLA-B haplotypes. Current HLA typing methods have limitations in resolution, accuracy, price, and/or convenience that prevent them from wide use for HLA-B*15:02 screening.

Briefly, there are four major approaches for HLA-B*15: 02 detection currently available:
(1) Direct sequencing methods—e.g., Sanger sequencing or next-generation sequencing (NGS)—are the most accurate options, but they are time-consuming, expensive, and also requiring special expertise to analyze the data;
(2) Sequence-specific oligonucleotide probe hybridization (SSOP) has high sensitivity and specificity, but it also has many disadvantages including complex processing and low resolution;
(3) Sequence-specific PCR (SSP-PCR), for example, the commercially available Pharmigene PG15:02 Detection Kit (U.S. Pat. No. 7,470,513), is less expensive and easier to process, but it is low throughput, and has low specificity owing to cross-reactions; and
(4) Tagging SNP method, in particular a two-SNP haplotype consisting of the minor alleles of rs2844682 and rs3909184, has been reported to tag the HLA-B*15:02 allele in 45 unrelated individuals from the HapMap (International HapMap, C., *The International HapMap Project*. Nature, 2003, 426(6968): pp. 789-96) population of Han Chinese in Beijing, China (CHB) (de Bakker et al., *A high-resolution HLA and SNP haplotype map for disease association studies in the extended human MHC*. Nat Genet, 2006, 38(10): pp. 1166-72). However, further testing has demonstrated these two SNPs have very poor accuracy (with ~6% sensitivity) to detect HLA-B*15:02 (Zhu, G. D., et al., *Genotypes at rs2844682 and rs3909184 have no clinical value in identifying HLA-B*15:02 carriers*. Eur J Clin Pharmacol, 2015).

Thus, in light of the potential for life-threatening adverse reactions caused by carbamazepine and related drugs, there is an urgent need for an accurate, high-throughput, and cost-effective assay for HLA-B*15:02 screening. In particular, an ideal assay should produce no false negatives. Such an assay would be highly valuable and immediately desired in clinical practice.

SUMMARY

The present disclosure is based on the surprising discovery of a particular SNP in the HLA-B*15:02 gene, rs144012689, which represents a strong biomarker for HLA-B*15:02. Accordingly, a new approach of detecting HLA-B*15:02 and thus, predicting, decreasing, and/or preventing carbamazepine (and its related drugs)—induced severe adverse skin reactions is provided.

In one aspect, provided herein is an isolated biomarker for the HIA-B*15:02 allele, comprising rs144012689. In some embodiments, the presence of the minor allele T on the minus strand indicates the presence of the HIA-B*15:02 allele.

Use of the biomarker is also provided, for predicting, decreasing and/or preventing adverse drug reactions induced by carbamazepine and its related drugs. In some embodiments, the adverse drug reactions comprise carbamazepine (and its related drugs)-induced severe adverse skin reactions.

Another aspect relates to a method for detecting the HLA-B*15:02 allele in a sample, comprising determining the presence of rs144012689 minor allele T in the sample. The method can optionally include a step of obtaining a sample. The method can, in some embodiments, further include subjecting the sample to an assay selected from the group consisting of TaqMan® genotyping, SNP array and next generation sequencing.

In certain embodiments, TaqMan® genotyping comprises subjecting the sample to a polymerase chain reaction in the presence of a Taq DNA polymerase, a pair of primers designated at the HLA-B gene such that an amplicon produced therefrom includes rs144012689, and a non-naturally modified probe that hybridizes with a portion of the amplicon at or near rs144012689. The probe can comprise one or more sequences selected from SEQ ID NO: 5, SEQ ID NO: 6, SEQ ID NO: 7, SEQ ID NO: 8, SEQ ID NO: 9 and/or SEQ ID NO: 10. In one embodiment, the method includes subjecting the sample to TaqMan® genotyping with three probes having the sequences of SEQ ID NO: 5, SEQ ID NO: 6, and SEQ ID NO: 7. In another embodiment, the method includes subjecting the sample to TaqMan® genotyping with three probes having the sequences of SEQ ID NO: 8, SEQ ID NO: 9 and SEQ ID NO: 10. In some embodiments, probe further contains a reporter dye and a quencher dye attached thereto such that when both attached, the quencher dye quenches a signal from the reporter dye, and when one or both of the reporter dye and the quencher dye is released from the probe, the reporter dye emits the signal. The signal may be fluorescence. One or both of the reporter dye and the quencher dye is capable of being released from the probe by Taq DNA polymerase when the probe is hybridized to the amplicon at or near rs144012689.

In certain embodiments, SNP array can be used which comprises a plurality of nucleic acids bound thereto, wherein the plurality of nucleic acids comprise one or more sequences selected from SEQ ID NO: 5, SEQ ID NO: 6, SEQ ID NO: 7, SEQ ID NO: 8, SEQ ID NO: 9 and/or SEQ ID NO: 10. DNA from the sample can be hybridized to the plurality of nucleic acids on the SNP array to detect the presence or absence of the SNP. In some embodiments, the DNA from the sample is fragmented and labeled with, e.g., a reporter dye.

In various embodiments, the sample can be from a patient in need of and prior to carbamazepine administration. The sample should comprise genomic DNA.

A further aspect relates to a non-naturally modified probe comprising a sequence selected from SEQ ID NO: 5, SEQ ID NO: 6, SEQ ID NO: 7, SEQ ID NO: 8, SEQ ID NO: 9 and/or SEQ ID NO: 10, wherein said probe has a detectable label attached thereto.

An additional aspect relates to a double-stranded nucleic acid molecule comprising a non-naturally modified probe and a target sequence complementary and annealed to the probe, wherein the probe comprises a sequence selected from SEQ ID NO: 5, SEQ ID NO: 6, SEQ ID NO: 7, SEQ ID NO: 8, SEQ ID NO: 9 and/or SEQ ID NO: 10, wherein said probe has a detectable label attached thereto.

Yet another aspect relates to a solid phase having a plurality of nucleic acids bound thereto, wherein the plurality of nucleic acids comprise one or more sequences selected from SEQ ID NO: 5, SEQ ID NO: 6, SEQ ID NO: 7, SEQ ID NO: 8, SEQ ID NO: 9 and/or SEQ ID NO: 10.

A further aspect relates to a solid phase having a plurality of nucleic acids bound thereto and a target sequence annealed to the nucleic acid, wherein the plurality of nucleic acids comprise one or more sequences selected from SEQ ID NO: 5, SEQ ID NO: 6, SEQ ID NO: 7, SEQ ID NO: 8, SEQ ID NO: 9 and/or SEQ ID NO: 10.

Another aspect relates to a method of treating a patient in need of carbamazepine, comprising: obtaining a sample from the patient; determining the presence or absence of rs144012689 minor allele T in the sample; and in the absence of rs144012689 minor allele T, administering carbamazepine to the patient.

Also provided herein is a kit for detecting the HLA-B*15:02 allele in a sample, comprising a probe selected from SEQ ID NO: 5, SEQ ID NO: 6, SEQ ID NO: 7, SEQ ID NO: 8, SEQ ID NO: 9 and/or SEQ ID NO: 10. In some embodiments, the kit can include three probes having the sequences of SEQ ID NO: 5, SEQ ID NO: 6, and SEQ ID NO: 7. In certain embodiments, the kit can include three probes having the sequences of SEQ ID NO: 8, SEQ ID NO: 9 and SEQ ID NO: 10. In various embodiments, the probe can be labeled by a fluorescent dye at the 5' terminus and a quencher at the 3' terminus. The probe can be suitable for a TaqMan® genotyping assay. The kit can further include a pair of primers designated at the HLA-B gene such that an amplicon produced therefrom includes rs144012689; dNTPs; and Taq DNA polymerase.

Each of the embodiments and aspects of the present disclosure can be practiced independently or combined. Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

These and other aspects of the present disclosure, as well as various advantages and utilities will be apparent with reference to the Detailed Description. Each aspect of the present disclosure can encompass various embodiments as will be understood.

All documents identified in this application are incorporated in their entirety herein by reference.

BRIEF DESCRIPTION OF THE DRAWINGS

FIG. 1 shows the results of an exemplary HLA-B*15:02 genotyping assay. NTC=no template control.

DETAILED DESCRIPTION

The presently disclosed methods and compositions cured the prior art deficiency and provide a novel biomarker rs144012689 and approach for HLA-B*15:02 screening. This approach is similar to but advantageous over the conventional tagging SNP method. Tagging SNPs are found in linkage disequilibrium with a certain haplotype but are not part of the gene haplotype itself. A limitation of tagging SNPs is that they rely on statistical inference of linkage and not necessarily empirically-defined linkage. Furthermore, it has been recently discovered that the currently-accepted tagging SNPs do not detect HLA-B*15:02 (Zhu, G. D., et al., *Genotypes at rs2844682 and rs3909184 have no clinical value in identifying HLA-B*15:02 carriers*. Eur J Clin Pharmacol, 2015). Unfortunately, due to the lack of quick and effective HLA-B*15:02 screening assays, as well as ignorance to the fact that rs2844682 and rs3909184 do not actually tag HLA-B*15:02, many laboratories still use these SNPs to define patient HLA-B*15:02 status, which have been shown to be highly error-prone (Zhu, G. D., et al., *Genotypes at rs2844682 and rs3909184 have no clinical value in identifying HLA-B*15:02 carriers*. Eur J Clin Pharmacol, 2015), or use the Pharmigene kit or simple SSP-PCR for low-resolution HLA-B*15:02 testing.

In contrast to the current tagging SNPs, the new SNP disclosed herein, rs144012689, resides in intron 5 of the HLA-B gene and is tightly associated with HLA-B*15:02 based on public databases. Furthermore, results from >25,000 patient samples using different detection assays show that rs144012689 is a reliable biomarker for HLA-B*15:02 with 100% sensitivity and 99.96% specificity. Additionally, a novel TaqMan® genotyping assay designed at the minor allele of rs144012689 has also shown a surprising 100% sensitivity and 100% specificity to detect HLA-B*15:02 after testing >1000 patient samples. Remarkably, rs144012689 completely eliminates false negatives, making it a highly valuable and clinically desirable biomarker. rs144012689-based detection is much more specific to HLA-B*15:02 than another currently commercialized method, such as the Pharmigene PG15:02 Detection Kit, whose product insert shows a list of false positives (HLA-B*15:13, B*15:31, B*15:55, B*15:88, B*15:89, B*18:20, B*95:12, B*95:21, B*95:44, and B*95:70). Thus, easy to process, high-throughput (e.g., at least 10, at least 20, at least 50, at least 100, or more samples in parallel), and cost-effective HLA-B*15:02 assays based on rs144012689 are provided herein. These assays can be used for highly sensitive screening for HLA-B*15:02 in patients requiring carbamazepine (or related drugs, e.g. phenytoin, lamotrigine, eslicarbazepine, fosphenytoin and oxcarbazepine) therapy to avoid potential life-threatening inflammatory adverse reactions in skin and mucous membranes.

Definitions

Various terms used throughout this specification shall have the definitions set forth herein.

"HLA" refers to the human leukocyte antigen system (HLA) complex that spans approximately 3.5 million base pairs located within the 6p21.3 region on the short arm of human chromosome 6 and contains more than 220 genes of diverse function. Many of the genes encode proteins of the immune system. The major regions are the class I and class II regions. The major Class I antigens are HLA-A, HLA-B, and HLA-C and the major Class II antigens are HLA-DP, HLA-DQ and HLA-DR. The HLA genes are among the most polymorphic genes in the genome. Polymorphisms that are expressed in the HLA antigen (and therefore of great interest for typing for transplantation) are localized primarily in exon 2 for the class II genes and exons 2 and 3 for the class I genes.

Each HLA allele name has a unique number corresponding to up to four sets of digits separated by colons. The digits before the first colon describe the type, which often corresponds to the serological antigen carried by an allotype. The next set of digits are used to list the subtypes, numbers being assigned in the order in which DNA sequences have been determined. Alleles whose numbers differ in the two sets of digits must differ in one or more nucleotide substitutions that change the amino acid sequence of the encoded protein. Alleles that differ only by synonymous nucleotide substitutions (also called silent or non-coding substitutions) within the coding sequence are distinguished by the use of the third set of digits. Alleles that only differ by sequence polymorphisms in the introns or in the 5' or 3' untranslated regions that flank the exons and introns are distinguished by the use of the fourth set of digits.

HLA-B*15:02 refers to a specific allele of the HLA-B gene in allele group 15 and having subtype 02. At least 9 synonymous substitutions, i.e., encoding the same protein, in the coding region (B*15:02:01-B*15:02:09) have been documented in the IMGT/HLA database (see www.ebi.ac.uk/cgi-bin/ipd/imgt/hla/allele.cgi).

As used herein, a "biomarker" refers to a measurable or detectable characteristic that provides information on presence and/or severity of a disease or compromised state in a patient; the relationship to a biological pathway; a pharmacodynamic or pharmacogenetic relationship or output; a companion diagnostic; a particular species; or a quality of a biological sample. Examples of biomarkers include genes, polymorphisms, proteins, peptides, antibodies, cells, gene products, enzymes, hormones, etc.

The term "gene" refers to a nucleic acid (e.g., DNA or RNA) sequence that comprises coding sequences necessary for the production of an RNA or a polypeptide or its precursor. The term "portion" when used in reference to a gene refers to fragments of that gene. The fragments may range in size from a few nucleotides to the entire gene sequence minus one nucleotide. The term "gene" also encompasses the coding regions of a structural gene and includes sequences located adjacent to the coding region on the 5' and/or 3' ends such that the gene corresponds to the length of the full-length mRNA. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "allele" as used herein generally refers to one of a plurality of species each encoding a similar sequence composition, but with a degree of distinction from each other. The distinction may include any type of genetic variation known to those of ordinary skill in the related art, that include, but are not limited to, polymorphisms such as single nucleotide polymorphisms (SNPs), insertions or deletions (the combination of insertion/deletion events are also referred to as "indels"), differences in the number of repeated sequences (also referred to as tandem repeats), and structural variations. For HLA alleles, typically, multiple genetic differences constitute an allele (i.e., most alleles differ from one another by more than one base). In reference to HLA genes, an allele is defined by the use of all of the digits in a current allele name.

The term "allele frequency" or "allelic frequency" as used herein generally refers to the proportion of all variants in a population that is comprised of a particular variant.

As used herein the word "haplotype" refers to a set of closely linked HLA alleles present on one chromosome which tend to be inherited together.

"Linkage disequilibrium" refers to the tendency of specific alleles at different genomic locations to occur together more frequently than would be expected by chance. Alleles at given loci are in complete equilibrium if the frequency of any particular set of alleles (or haplotype) is the product of their individual population frequencies.

The term "polymorphism" refers to the occurrence of two or more alternative genomic sequences or alleles between or among different genomes or individuals. The variation may comprise but is not limited to one or more base changes, the insertion of one or more nucleotides or the deletion of one or more nucleotides. A polymorphism includes a single nucleotide polymorphism (SNP), a simple sequence repeat (SSR) and indels, which are insertions and deletions.

As used herein, the term "single nucleotide polymorphism" also referred to by the abbreviation "SNP" means a polymorphism at a single site wherein the polymorphism constitutes a single base pair change. SNP is a common form of genetic polymorphisms. SNP may influence gene functions and modifies an individual's susceptibility to diseases. Almost any diseases have a genetic component in its etiology and most are being unraveled in genetic association studies. In some instances, a single SNP may be sufficient to confer susceptibility, while in others multiple SNPs may act jointly to influence disease susceptibility. An estimated 20 million SNPs are present in human genome.

One of a skilled artisan understands that SNPs typically have two and up to four alternative alleles, and each corresponds to a nucleotide that may exist in the chromosome. Thus, a SNP is characterized by two or more nucleotides out of four (A, C, G, T). An example would be that a SNP has either allele C or allele T at a given position on each chromosome. This is shown as C>T or C/T. The more commonly occurring allele is shown first (in this case, it is C) and called the major, common or wild-type allele. The alternative allele that occurs less commonly instead of the common allele (in this case, it is T) is called minor, rare or variant allele. Since humans are diploid organisms meaning that each chromosome occurs in two copies, each individual has two alleles at a SNP. These alleles may be two copies of the same allele (CC or TT) or they may be different ones (CT). The CC, CT and TT are called genotypes. Among these CC and TT are characterized by having two copies of the same allele and are called homozygous genotypes. The genotype CT has different alleles on each chromosome and is a heterozygous genotype. Individuals bearing homozygote or heterozygote genotypes are called homozygote and heterozygote, respectively.

"rs144012689" is a SNP located on human chromosome 6 position 31355003. intron 5 of the HILA-B gene. On the minus strand, the major allele is A and the minor allele is T.

The term "genotype" refers to a description of the alleles of a gene contained in an individual or sample. As used herein, "genotyping" a subject (or DNA or other biological sample) for a polymorphic allele of a gene(s) means detecting which allelic or polymorphic form(s) of the gene(s) or gene expression products (e.g., heterogeneous nuclear (hn) RNA, messenger RNA or protein) are present or absent in a subject (or a sample). Related RNA or protein expressed from such genes may also be used to detect polymorphic variation. As is well known in the art, an individual may be heterozygous or homozygous for a particular allele. More than two allelic forms may exist, thus there may be more than three possible genotypes. For purposes of the present disclosure, "genotyping" includes the determination of HLA, in particular HLA-B alleles using suitable serologic, histologic or molecular techniques among others, as are known in the art or as disclosed herein. As used herein, an allele may be "detected" or "determined" when its identity (e.g., sequence) is known. Sequence variations may be detected directly (by, e.g., sequencing) or indirectly (e.g., by restriction fragment length polymorphism analysis, or detection of the hybridization of a probe of known sequence, or reference strand conformation polymorphism), or by using other known methods.

The term "sample" refers to any composition containing or presumed to contain nucleic acid (e.g., DNA) from an individual. In the context of the present disclosure, any type of body sample may be used, including without limitation, skin, buccal swab, tissue biopsy, plasma, serum, whole blood and blood components, saliva, urine, tears, seminal fluid, vaginal fluids and other fluids and tissues, including paraffin embedded tissues or tissues collected and preserved in the course of a forensic investigation. Samples also may include constituents and components of in vitro cultures of cells obtained from an individual. DNA can be extracted from various samples for genotyping etc.

The term "primer" refers to an oligonucleotide that acts as a point of initiation of DNA synthesis in a PCR reaction. A primer is usually about 15 to about 40 nucleotides in length (or shorter or longer) and typically includes at least one target-hybridized region that is at least substantially complementary to the target sequence.

The term "probe" refers to an oligonucleotide that hybridizes to a target sequence on a target nucleic acid. Target sequence refers to a region of nucleic acid that is to be analyzed and comprises the polymorphic site of interest. For TaqMan® assays, the probe can additionally contain a quencher and a dye (e.g., fluorescent). When the probes are intact, fluorescence is suppressed because the quencher dyes are in the proximity of the reporter dyes. At least two probes can be included in one TaqMan® assay; one for the major allele, and the other for the minor allele in a two-allele system. More probes can be included if there are more than two alleles within the target region.

The term "TaqMan® genotyping" or "TaqMan® assay" is a technology that exploits the 5'-3' nuclease activity of Taq DNA polymerase to allow direct detection of the PCR product by the release of a fluorescent report from a probe as a result of PCR. The TaqMan® assay permits discrimination between the alleles of a two-allele (or more) system. It represents a sensitive and rapid means of genotyping SNPs. A typical TaqMan assay includes a Taq DNA polymerase, dNTPs, a pair of primers designed to amplify a target region, and at least two probes each hybridizing to a different allele within the target region, mixed with DNA samples and subjected to PCR (e.g., real-time PCR that can detect and measure fluorescence). In the PCR annealing step, the probes hybridize to the targeted site. During PCR extension, the reporter and quencher dyes are released due to the 5' nuclease activity of the Taq polymerase, resulting in an increased characteristic fluorescence of the reporter dye. Exonuclease activity only happens on the perfectly hybridized probes, since a probe containing a mismatched base will not be recognized by the Taq polymerase.

"Taq DNA polymerase" refers to a heat stable enzyme used in the polymerase chain reaction (PCR) to amplify target DNA. It was discovered in bacterium *Thermus aquaticus* and hence the name. It should be noted that other polymerases having 5'-3' nuclease activity can also be used to replace the Taq DNA polymerase in TaqMan assays.

"Next Generation Sequencing" or "NGS" includes one or more of 454-based sequencing (Roche), Genome Analyzer-based sequencing (Illumina/Solexa), Ion torrent: Proton/PGM sequencing and ABI-SOLiD-based sequencing (Applied Biosystems). The basic chemistry relies on the fact that DNA polymerase catalyzes the incorporation of dNTPs into a DNA polymer during sequential cycles of DNA synthesis. During each cycle, the nucleotide being incorporated is either identified by an optical signal (e.g., fluorophore excitation) or change in pH (incorporation of each base releases a proton). Compared to conventional sequencing such as Sanger sequencing, the critical difference is that, instead of sequencing a single DNA fragment at a time, NGS extends the process across of multiple fragments in a parallel fashion, greatly enhancing sequencing speed and accuracy.

The term "nucleic acid" or "oligonucleotide" or "polynucleotide" refers to polymers of nucleotides (e.g., ribonucleotides or deoxyribonucleotides) both natural and non-natural. The term is not limited by length (e.g., number of monomers) of the polymer. A nucleic acid may be single-stranded or double-stranded and will generally contain 5'-3' phosphodiester bonds, although in some cases, nucleotide analogs may have other linkages. Nucleic acids may include naturally occurring bases (adenosine, guanidine, cytosine, uracil and thymidine) as well as non-natural bases. The term "non-natural nucleotide" or "modified nucleotide" refers to a nucleotide that contains a modified nitrogenous base, sugar or phosphate group, or that incorporates a non-natural moiety in its structure. Examples of non-natural nucleotides include dideoxynucleotides, biotinylated, aminated, deaminated, alkylated, benzylated and fluorophor-labeled nucleotides.

The terms "complementary" and "complementarity" refer to polynucleotides (e.g., a sequence of nucleotides) related by the base-pairing rules. For example, for the sequence 5'-A-G-T-3' is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

Carbamazepine or CBZ, also known as Tegretol, Tegol, G-32883, Biston, Calepsin, Carbatrol, Epitol, Finlepsin, Sirtal, Stazepine. Telesmin, or Timonil, is an aromatic anticonvulsant. Carbamazepine is widely used to treat epileptic seizures and trigeminal neural-gia (causes facial nerve pain). While not indicated for treatment in the FDA label, this medication may also be used to treat bipolar disorder.

An "adverse drug reaction" (ADR) is an undesired and unintended effect of a drug. In particular, an adverse drug reaction occurs at doses used for prophylaxis, diagnosis or therapy. According to a widely cited meta-analysis, ADRs were ranked between the fourth and sixth most common cause of death (Lazarou et al., JAMA, 279(15): 1200-1205, 1998). Cutaneous ADRs account for about 2-3% of all hospital admissions (Bigby et al., JAMA, 256(24):3358-3363, 1986). They range from mild maculopapular (MPE), with increasing severity, to life-threatening ADRs, such as hypersensitivity syndrome (HSS), Stevens-Johnson syndrome (SJS) and toxic epidermal necrolysis (TEN; Lyell's syndrome). The mortality rate of the latter can be as high as 40%.

"Carbamazepine-induced severe adverse skin reactions" refers to the adverse drug reactions induced by carbamazepine, in particular cutaneous adverse reactions. In general, these hypersensitivity reactions include fever, rash, immune cell (white blood cells) abnormalities, and in some cases, hepatitis. The most severe adverse reactions include skin blistering injuries called Stevens-Johnson syndrome (SJS) and toxic epidermal necrolysis (TEN). Carbamazepine-induced SJS/TEN is rare among Europeans, with a reported risk of 1-6 per 10,000 individuals exposed to the drug. The risk is almost 10-100 folds higher in Asian countries where the HLA-B*15:02 allele is prevalent (Lonjou et al., 2006; "Tegretol® and Tegretol®-XR prescribing information: FDA approved labeling," 2014). The strongest association between the risk of developing SJS/TEN upon carbamazepine therapy and a person's genetic make-up has been found for HLA-B*5:02 allele in Asians (see Chung et al., Medical genetics: a marker for Stevens-Johnson syndrome, Nature, 2004, 428(6982): p. 486; Chen et al., Carbamazepine-induced toxic effects and HLA-B*15:02 screening in Taiwan, N Engl J Med, 2011, 364(12): pp. 1126-33; and Mushiroda and Nakamura, Genome Medicine 2011, 3:28).

SJS and TEN are immune-complex-mediated hypersensitivity disorders characterized by rapid development of blistering exanthema of purpuric macules and target-like lesions accompanied with mucules involvement and skin detachments (Roujeau et al. J Invest Dermatol, 1994, 102:28 S-30S). They are caused mostly by drugs, such as sulfonamides, anticonvulsants, allopurinol, nonsteroidal anti-inflammatory drugs, and antimalarials (Roujeau et al., N. Engl. J. Med., 333(24):1600-1607, 1995).

HLA-B*15:02 and CBZ

The HLA-B*15:02 allele is present in global populations at about 0.9% allele frequency based on publicly available databases (Table 1). However, the frequencies of alleles at the HLA loci vary remarkably depending on ethnicity. In the case of HLA-B*15:02, the allele exists in Han Chinese at a frequency of 8.6% (Chung W H. et al. Nature. 2004 Apr. 1; 428(6982):486), while it exists in Japanese and Koreans at a frequency of only 0.1%; Caucasians and Africans also have very low frequency (www.allelefrequencies.net). In overall Asian populations, the HLA-B*15:02 allele frequency is about 3.9% (Table 1).

In terms of CBZ, a research using Taiwanese subjects demonstrated that the HLA-B*15:02 allele is very strongly associated with SJS and TEN induced by CBZ (Chung W H. et al. Nature. 2004 Apr. 1; 428(6982):486). Thus, HLA-B*15:02 screening is warranted in patients requiring carbamazepine therapy (Tegretol® and Tegretol-XR prescribing information: FDA approved labeling. 2014). Currently, the detection of HLA-B*15:02 through HLA typing is feasible but technically challenging primarily due to the lack of reliable biomarkers or limitations in resolution, accuracy, price, and convenience. An ideal biomarker should be able to distinguish HLA-B*15:02 from other highly homologous HLA-B alleles; should be as sensitive as possible to avoid false negatives; and can be adopted into various detection assays.

It should be noted that other aromatic anticonvulsants, including phenytoin, lamotrigine, eslicarbazepine, fosphenytoin and oxcarbazepine cause similar ADRs as CBZ. Therefore, HLA-B*15:02 can be employed to assess the risk for ADRs to these other aromatic anticonvulsants as well. The aromatic anticonvulsants for which HLA-B*15:02 can be used as a risk factor also include compounds or metabolites of CBZ phenytoin, lamotrigine, eslicarbazepine, fosphenytoin and oxcarbazepine. Metabolites of these drugs are known in the art (see, e.g., Gennis et al., 1991; Leeder, Epilepsia, 39 Suppl. 7:S8-16, 1998; Naisbitt et al., Mol. Pharmacol., 63(3):732-741, 2003), such as CBZ-10,11 epoxide, CBZ-10,11-diol, CBZ-2,3-diol, dihydro CBZ, CBZ catechol and CBZ o-quinone, p-hydroxy phenyloin, phenyloin dihydrodiol, phenyloin catechol, phenyloin methylcatechol, and phenyloin o-quinone.

Rs144012689 as a Biomarker for HLA-B*15:02

Using a deep bioinformatics analysis of the HLA-B locus by mining public databases and sequence data of patient samples, we identified a series of regions that would allow us to hone in on the B*15:02 allele specifically. Specifically, the 344 known HLA-B haplotypes (www.hla.alleles.org/data/txt/b_gen.txt) and additional 9 HLA-B*15:02 silent mutations (B*15:02:01-B*15:02:09) were compared using in-house mining algorithms, and the SNP rs144012689 located at intron 5 of HLA-B was discovered to be present in HLA-B*15:02 and not in the vast majority of other alleles. On the minus strand, the major allele of rs144012689 is A, and the minor allele is T. Only HLA-B*15:02 and HLA-B*15:13 contain the variant SNP of "T" at rs144012689, all the other HLA-B haplotypes contain the wild-type SNP of "A" at that location. Thus, if rs144012689 is an accurate marker for detection of HLA-B*15:02 and the risk for CBZ usage implied by the presence of this allele, the only known false positive for detection is HLA-B*15:13, which has an allele frequency of about 9 times less than HLA-B*15:02 (www.allelefrequencies.net; Table 1). Thus, we posited that rs144012689 could act as a reliable marker for HLA-B*15:02, as shown below.

TABLE 1

HLA-B*15:02 and HLA-B*15:13 Allele Frequencies

| Allele | Allele Frequency in Global Populations | Allele Frequency in Asians | Allele Frequency in Caucasians | Allele Frequency in Africans | Data Source |
|---|---|---|---|---|---|
| HLA-B*15:02 | 0.91% (n = 2,453,203) | 3.92% (n = 560,842) | 0.001% (n = 1,325,156) | 0.21% (n = 41,314) | www.allelefrequencies.net |
| HLA-B*15:13 | 0.08% (n = 2,145,939) | 0.43% (n = 353,749) | 0.0002% (n = 1,288,839) | 0.04% (n = 8,540) | |

First, the allele frequencies of rs144012689 minor allele (A>T) and HLA-B*15:02 were found similar in global populations as well as in Asians, Caucasians, and Africans (Table 2).

TABLE 2

The allele frequencies of rs144012689 minor allele and HLA-B*15:02 are similar.

| Allele | Allele Frequency in Global Populations | Allele Frequency in Asians | Allele Frequency in Caucasians | Allele Frequency in Africans | Data Source |
|---|---|---|---|---|---|
| Rs144012689 | 1.8% (n = 5,008) | 4.6% (n = 1,986) | 0% (n = 1,066) | 0% (n = 1,322) | 1000 Genomes Project |
| HLA-B*15:02 | 0.91% (n = 2,453,203) | 3.92% (n = 560,842) | 0.001% (n = 1,325,156) | 0.21% (n = 41,314) | www.allelefrequencies.net |

Next, we tested the correlation between rs144012689 minor allele and HLA-B*15:02 allele by comparing the genotyping results from publicly available databases. The rs144012689 genotype results and HLA-B typing results of the 1000 Genomes Project samples were retrieved from the 1000 Genomes Browser and NCBI dbMHC portal (in which HLA typing was done by standard Sanger sequencing), respectively. Specifically, the HLA-B*15:02 genotyping results were known as 'positive' if one or two copies of HLA-B*15:02 were present or as 'negative' if no copies of HLA-B*15:02 were present, and there was no intermediate genotype. Overall, 100% concordance was observed between rs144012689 minor allele positives (samples containing the 'T' (minor) allele on the minus strand) and HLA-B*15:02 positives in all 955 samples. As shown in Table 3, among these 995 samples, there were 12 true positive (TP) samples that were heterozygous for rs144012689 minor allele which were also positive for the HLA-B*15:02 allele. There were 943 true negative (TN) samples that were negative for rs144012689 minor allele (these samples contained A/A on the minus strand; A is the major allele) and were negative for the HLA-B*15:02 allele. There were no false positives (FP; samples that were positive for rs144012689 minor allele but negative for HLA-B*15:02) or false negatives (FN; samples that were negative for rs144012689 minor allele but positive for HLA-B*15: 02) in these 955 samples. This result shows 100% accuracy (100% sensitivity and 100% specificity) for the correlation of HLA-B*15:02 with the rs144012689 minor allele. This correlation is statistically significant (P=0.0001 by two-tailed Fisher's exact test).

TABLE 3 rs144012689 minor allele positives are also HLA-B*15:02 positive

| rs144012689 (minus strand, from the 1000 Genomes Project) | HLA-B*15:02 (from NCBI dbMCH portal) | | Sensitivity | Specificity | PPV | NPV | P-value* |
|---|---|---|---|---|---|---|---|
| | + | − | | | | | |
| T/A (T is the minor allele) | TP (12) | FP (0) | 100% | 100% | 100% | 100% | 0.0001 |
| A/A (homozygote major allele) | FN (0) | TN (943) | | | | | |

TP (true positive) = samples that were positive for both rs144012689 minor allele and HLA-B*15:02
FP (false positive) = samples that were positive for rs144012689 minor allele and were negative for HLA-B*15:02
FN (false negative) = samples that were negative for rs144012689 minor allele but were indeed positive for HLA-B*15:02
TN (true negative) = samples that were negative for rs144012689 minor allele and were also negative for HLA-B*15:02
PPV = positive predictive value;
NPV = negative predictive value;
*P value was calculated by two-tailed Fisher's exact-test.

To further verify the correlation between rs144012689 minor allele and HLA-B*15:02, we then sequenced thousands of patient samples using NGS for both HLA-B exon 2/3 and intron 5 to generate conventional HLA-B genotyping and rs144012689 genotyping, respectively (NGS services performed by HistoGenetics LLC, Ossining, N.Y.). In the cohort of >25,000 patient samples, rs144012689 minor allele shows 100% sensitivity and 99.96% specificity to detect HLA-B*15:02, with no false negatives detected. There were 9 false positives detected, all of which were HLA-B*15:13, as expected from our previous information (Table 4).

TABLE 4 rs144012689 minor allele is correlated with HLA-B*15:02 allele in MH patient samples

| rs144012689 (minus strand, from HGX NGS sequencing) | HLA-B*15:02 (HGX NGS sequencing) | | Sensitivity | Specificity | PPV | NPV | P-value* |
|---|---|---|---|---|---|---|---|
| | + | − | | | | | |
| T/A (T is the minor allele) | TP (51) | FP (9) | 100% | 99.96% | 85% | 100% | 0.0001 |
| A/A (A is the major allele) | FN (0) | TN (25,604) | | | | | |

TP (true positive) = samples that were positive for both rs144012689 minor allele and HLA-B*15:02
FP (false positive) = samples that were positive for rs144012689 minor allele and were negative for HLA-B*15:02
FN (false negative) = samples that were negative for rs144012689 minor allele but were indeed positive for HLA-B*15:02
TN (true negative) = samples that were negative for rs144012689 minor allele and were also negative for HLA-B*15:02
PPV = positive predictive value;
NPV = negative predictive value;
*P value was calculated by two-tailed Fisher's exact-test.

Significantly and remarkably, there are no false negatives from >25,000 patient samples tested, proving that rs144012689 is a powerful and accurate biomarker for HLA-B*15:02. This is because if a patient is falsely identified as HLA-B*15:02 negative and given the drug (CBZ and related drugs), they are at risk of the potentially lethal adverse drug reaction (SJS/TEN). As such, false negatives must be avoided in an ideal HLA-B*15:02 screening assay. However, currently available markers such as rs2844682 and rs3909184 have been found to have very poor accuracy and are unable to avoid false negatives (Zhu, G. D., et al., *Genotypes at rs2844682 and rs3909184 have no clinical value in identifying HLA-B*15:02 carriers*. Eur J Clin Pharmacol, 2015). In contrast, rs144012689 is a strong biomarker for HLA-B*15:02 and can be detected using various genotyping methods.

HLA-B Genotyping

In one aspect the genotype of HLA-B can be measured by determining the DNA polynucleotide sequence (e.g., intron 5 of HLA-B) using any suitable technique as is known in the art. Polynucleotides utilized for typing are typically genomic DNA, or a polynucleotide fragment derived from a genomic polynucleotide sequence, such as in a library made using genomic material from the individual. Determination of the presence of rs144012689 can be performed by analyzing a nucleic acid sample present in a biological sample obtained from an individual. The nucleic acid may be isolated from blood samples, cells or tissues. Protocols for isolation of nucleic acid are known.

As appreciated by one of skill in the art, various suitable genotyping assays may be used in the present disclosure. This includes hybridization using allele-specific oligonucleotides, primer extension, allele-specific ligation, sequencing (e.g., pyrosequencing), electrophoretic separation techniques, single-base extension assay, DNA microarray, high-resolution melting method, denaturing high-performance liquid chromatography, mass spectrometry, microsphere-based suspension array platform (Luminex)-based assays and the like. Exemplary assays include 5' nuclease assays, molecular beacon allele-specific oligonucleotide assays, and SNP scoring by real-time pyrophosphate sequences. Other suitable methods that are known in the art can also be used in the present disclosure to detect the presence of SNP.

In some embodiments, the polymorphism may be detected in a method that comprises contacting a polynucleotide sample from an individual with a specific binding agent for the polymorphism and determining whether the agent binds to the polynucleotide, where the binding indicates that the polymorphism is present. The binding agent may also bind to flanking nucleotides on one or both sides of the polymorphism, for example at least 2, 5, 10, 15 or more flanking nucleotide in total or on each side. In the case where the presence of the polymorphism is being determined in a polynucleotide it may be detected in the double stranded form, but is typically detected in the single stranded form.

The binding agent may be a polynucleotide (single or double stranded) typically with a length of at least 10 nucleotides, for example at least 15, 20, 30, or more nucleotides. A polynucleotide agent which is used in the method will generally bind to the polymorphism of interest, and the flanking sequence, in a sequence specific manner (e.g. hybridize in accordance with Watson-Crick base pairing) and thus typically has a sequence which is fully or partially complementary to the sequence of the polymorphism and flanking region. The binding agent may be a molecule that is structurally similar to polynucleotides that comprises units (such as purine or pyrimidine analogs, peptide nucleic acids, or RNA derivatives such as locked nucleic acids (LIMA)) able to participate in Watson-Crick base pairing. The agent may be a protein, typically with a length of at least 10 amino acids, such as at least 20, 30, 50, or 100 or more amino acids. The agent may be an antibody (including a fragment of such an antibody that is capable of binding the polymorphism).

In one embodiment of the present methods a binding agent is used as a probe. The probe may be labeled or may be capable of being labeled indirectly. The detection of the label may be used to detect the presence of the probe on (bound to) the nucleic acid of the individual. The binding of the probe to the polynucleotide may be used to immobilize either the probe or the polynucleotide (and thus to separate it from one composition or solution). In another embodiment the polynucleotide of the individual is immobilized on a solid support and then contacted with the probe. The presence of the probe immobilized to the solid support (via its binding to the polymorphism) is then detected, either directly by detecting a label on the probe or indirectly by contacting the probe with a moiety that binds the probe. In the case of detecting a polynucleotide polymorphism the solid support is generally made of nitrocellulose or nylon.

In some embodiments a non-naturally modified probe can be used. The probe can be artificially modified to have a detectable label or dye attached thereto and hence is non-naturally occurring. The probe can contain a sequence selected from SEQ ID NO: 5, SEQ ID NO: 6, SEQ ID NO: 7, SEQ ID NO: 8, SEQ ID NO: 9 and/or SEQ ID NO: 10. The detectable label or dye can be covalently, non-covalently, directly, or indirectly attached to the probe. The label can be fluorescent or non-fluorescent (e.g., haptens such as Biotin and Digoxigenin). Commonly used fluorescent labels that are known in the art include rhodamine, fluorescein and cyanine their derivatives, ATTO, Eterneon™, Alexa Fluor®, Dy, Cy3™, Cy3.5™, Cy5™, Cy5.5™, HEX, TET, FAM, VIC and Dabcyl. These fluorescent labels can be directly detected via, e.g., fluorescence spectroscopy. Biotin and Digoxigenin are indirect labels since their visualization requires a secondary reporter molecule, Streptavidin and Digoxigenin antibody, respectively. Labels can be attached post-synthetically to the 5'-terminus of an oligonucleotide via an amino- or thiol-linker with a 6-Carbon spacer arm. The dye can also be coupled directly during synthesis via its phosphoramidite. Postsynthetic labeling of oligonucleotides at internal sites of the sequence is possible by substituting any thymidine with 5-C6-Amino-2'-deoxythymidine. In addition, all other bases can be substituted if required. It is also possible to label the 3'-end of oligonucleotides post-synthetically via an amino link. The labeled or unlabeled probes can be used in one or more of: direct binding assay, SNP array, and TaqMan® genotyping.

The present methods may be based on an oligonucleotide ligation assay in which two oligonucleotide probes are used. These probes bind to adjacent areas on the polynucleotide which contains the polymorphism, allowing (after binding) the two probes to be ligated together by an appropriate ligase enzyme. However the two probes will only bind (in a manner which allows ligation) to a polynucleotide that contains the polymorphism, and therefore the detection of the ligated product may be used to determine the presence of the polymorphism.

In one embodiment the probe is used in a heteroduplex analysis based system to detect polymorphisms. In such a system when the probe is bound to a polynucleotide sequence containing the polymorphism, it forms a heteroduplex at the site where the polymorphism occurs (i.e. it does not form a double strand structure). Such a heteroduplex structure can be detected by the use of an enzyme that is single or double strand specific. Typically the probe is an RNA probe and the enzyme used is RNAse H that cleaves the heteroduplex region, thus allowing the polymorphism to be detected by means of the detection of the cleavage products.

The method may be based on fluorescent chemical cleavage mismatch analysis which is described for example in PCR Methods and Applications 3:268-71 (1994) and Proc. Natl. Acad. Sci. 85:4397-4401 (1998). In one embodiment the polynucleotide agent is able to act as a primer for a PCR reaction only if it binds a polynucleotide containing the polymorphism (i.e. a sequence- or allele-specific PCR system). Thus a PCR product will only be produced if the polymorphism is present in the polynucleotide of the individual, and the presence of the polymorphism is determined by the detection of the PCR product. Preferably the region of the primer which is complementary to the polymorphism is at or near the 3' end the primer. In one embodiment of this system the polynucleotide agent will bind to the wild-type sequence but will not act as a primer for a PCR reaction.

The method may be a Restriction Fragment Length Polymorphism (RFLP) based system. This can be used if the presence of the polymorphism in the polynucleotide creates or destroys a restriction site that is recognized by a restriction enzyme. Thus treatment of a polynucleotide that has such a polymorphism will lead to different products being produced compared to the corresponding wild-type sequence. Thus the detection of the presence of particular restriction digest products can be used to determine the presence of the polymorphism. For example, PCR-RFLP is technique to detect a variation in the DNA sequence of a genome by restriction endonuclease digestion of the PCR product and analyzing the size of the resulting fragments by gel electrophoresis.

The presence of the polymorphism may be determined based on the change that the presence of the polymorphism makes to the mobility of the polynucleotide or protein during gel electrophoresis. In the case of a polynucleotide single-stranded conformation polymorphism (SSCP) analysis may be used. This measures the mobility of the single stranded polynucleotide on a denaturing gel compared to the corresponding wild-type polynucleotide, the detection of a difference in mobility indicating the presence of the polymorphism. Denaturing gradient gel electrophoresis (DGGE) is a similar system where the polynucleotide is electrophoresed through a gel with a denaturing gradient, a difference in mobility compared to the corresponding wild-type polynucleotide indicating the presence of the polymorphism.

The presence of the polymorphism may be determined using a fluorescent dye and quenching agent-based PCR assay such as the TaqMan® PCR detection system. In another method of detecting the polymorphism a polynucleotide comprising the polymorphic region is sequenced across the region which contains the polymorphism to determine the presence of the polymorphism.

The Peptide Nucleic Acid (PNA) affinity assay is a derivative of traditional hybridization assays (Nielsen et al., Science 254:1497-1500 (1991); Egholm et al., J. Am. Chem. Soc. 1 14:1895-1897 (1992); James et al., Protein Science 3:1347-1350 (1994)). PNAs are structural DNA mimics that follow Watson-Crick base pairing rules, and are used in standard DNA hybridization assays. PNAs display greater specificity in hybridization assays because a PNA/DNA mismatch is more destabilizing than a DNA/DNA mismatch and complementary PNA/DNA strands form stronger bonds than complementary DNA/DNA strands.

DNA microarrays have been developed to detect genetic variations and polymorphisms (Taton et al., Science 289: 1757-60, 2000; Lockhart et al., Nature 405:827-836 (2000); Gerhold et al., Trends in Biochemical Sciences 24:168-73 (1999); Wallace, R. W., Molecular Medicine Today 3:384-89 (1997); Blanchard and Hood, Nature Biotechnology 149: 1649 (1996)). DNA microarrays are fabricated by high-speed robotics, on glass or nylon substrates, and contain DNA fragments with known identities ("the probe"). The microarrays are used for matching known and unknown DNA fragments ("the target") based on traditional base-pairing rules. The Protein Truncation Test (PTT) is also commonly used to detect genetic polymorphisms (Roest et al., Human Molecular Genetics 2:1719-1721 (1993); Van Der Luit et al., Genomics 20:1-4 (1994), Hogervorst et al., Nature Genetics 10: 208-212 (1995)). Typically, in the PTT, the gene of interest is PCR amplified, subjected to in vitro transcription/translation, purified, and analyzed by polyacrylamide gel electrophoresis.

In one embodiment, a SNP array can be used to detect rs144012689. An array containing immobilized allele-specific oligonucleotide probes can be designed. In certain embodiments, the probes can contain one or more sequences selected from SEQ ID NO: 5, SEQ ID NO: 6, SEQ ID NO: 7, SEQ ID NO: 8, SEQ ID NO: 9 and/or SEQ ID NO: 10. Target nucleic acid sequences can be obtained from samples, fragmented and labeled with, e.g., fluorescent dyes. Then the target nucleic acid sequences can be allowed to hybridize with probes on the array. In one embodiment, hybridization condition is controlled to be stringent so as to only allow binding with 100% complementarity. A detection system that records and interprets the hybridization signal is used to detect hybridization thereby ascertaining the allele present in the sample.

Various other detection techniques suitable for use in the present methods will be apparent to those conversant with methods of detecting, identifying, and/or distinguishing polymorphisms. Such detection techniques include but are not limited to direct sequencing, use of "molecular beacons" (oligonucleotide probes that fluoresce upon hybridization, useful in real-time fluorescence PCR; see e.g., Marras et al., Genet Anal 14:151 (1999)); electrochemical detection (reduction or oxidation of DNA bases or sugars; see U.S. Pat. No. 5,871,918 to Thorp et al.); rolling circle amplification (see, e.g., Gusev et al., Am J Pathol 159:63 (2001)); Third Wave Technologies (Madison Wis.) INVADER® non-PCR based detection method (see, e.g., Lieder, Advance for Laboratory Managers, 70 (2000)). Accordingly, any suitable detection technique as is known in the art may be utilized in the present methods.

Conventional molecular biology, microbiology, and recombinant DNA techniques including sequencing techniques are well known among those skilled in the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook, et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984); F. M. Ausubel, et al. (eds.), Current Protocols in Molecular Biology, John Wiley & Sons, Inc. (1994).

The sequence of any nucleic acid including a gene or PCR product or a fragment or portion thereof may be sequenced by any method known in the art (e.g., chemical sequencing or enzymatic sequencing). "Chemical sequencing" of DNA may denote methods such as that of Maxam and Gilbert (1977) (Proc. Natl. Acad. Sci. USA 74:560), in which DNA is randomly cleaved using individual base-specific reactions. "Enzymatic sequencing" of DNA may denote methods such as that of Sanger (Sanger, et al., (1977) Proc. Natl. Acad. Sci. USA 74:5463).

In particular, next-generation sequencing enables researchers to obtain large amounts of data at a reduced cost and thus provides a tremendous opportunity to genotype an individual of any species in depth (Lai et al., "Genome-wide patterns of genetic variation among elite maize inbred lines" 2010, Nat Genet 42: 1027-1030). Recently, several genotyping-by-sequencing (GBS) approaches were developed to genotype hundreds of individuals simultaneously (Andolfatto et al. "Multiplexed shotgun genotyping for rapid and efficient genetic mapping" 2011, Genome Res 21: 610-17; Baird et al. "Rapid SNP discovery and genetic mapping using sequenced RAD markers" 2008, PLoS One 3: e3376; Elshire et al. "A Robust, Simple Genotyping-by-Sequencing (GBS) Approach for High Diversity Species" 2011 PLoS One 6(5): e19379).

Once the nucleic acid is obtained, amplified, and/or fragmented, it can be sequenced using any appropriate sequencing techniques. For example, adaptors can be added to the nucleic acid which is then subjected to, for example, Illumina®-based sequencing techniques. Such adaptors can provide each fragment to which they are added with a known sequence designed to provide a binding site for a primer that is used during the sequencing process. Other examples of sequencing techniques that can be used include, without limitation, Sanger sequencing, Next Generation Sequencing (NGS or second generation sequencing), high-throughput sequencing, ultrahigh-throughput sequencing, ultra-deep sequencing, massively parallel sequencing, 454-based sequencing (Roche), Genome Analyzer-based sequencing (Illumina/Solexa), Ion torrent: Proton/PGM sequencing and ABI-SOLiD-based sequencing (Applied Biosystems).

Briefly, in Genome Analyzer-based sequencing (or Illumina sequencing), the input sample is cleaved into 100-150 bp reads. The fragments are ligated to generic adaptors and attached to a slide. PCR is carried out to amplify each read using adaptor-specific primers, creating a spot with many copies of the same read, which are then separated into single strands to be sequenced. The slide is flooded with nucleotides and DNA polymerase. These nucleotides are fluorescently labelled, with a different color corresponding to a different base. The nucleotides also have a terminator, so that only one base is added at a time. An image is taken of the slide at each cycle. In each read location, there will be a fluorescent signal indicating the base that has been added. The slide is then prepared for the next cycle. The terminators are removed, allowing the next base to be added, and the fluorescent signal is removed, preventing the signal from contaminating the next image. The process is repeated, adding one nucleotide at a time and imaging in between. Computers are then used to detect the base at each site in each image and these are used to construct a sequence.

In Roche 454-based sequencing the nuclei acids are fragmented into up to 1 kb reads. Generic adaptors are added to the ends and attached to beads, one DNA fragment per bead. The fragments are then amplified by PCR using adaptor-specific primers. Each bead is then placed in a single well of a slide. The wells also contain DNA polymerase and sequencing buffers. The slide is flooded with one of the four dNTP species. Where this nucleotide is next in the sequence, it is added to the sequence read. If that single base repeats, then more will be added. The addition of each nucleotide releases a light signal. These locations of signals are detected and used to determine which beads the nucleotides are added to. Then the dNTP mix is washed away. The next dNTP mix is now added and the process repeated, cycling through the four dNTPs. Graphs for each sequence read are generated, showing the signal density for each nucleotide wash. The sequence can then be determined computationally from the signal density in each wash.

Ion torrent and Ion proton sequencing exploit the fact that addition of a dNTP to a DNA polymer releases an H+ ion. First, the input DNA or RNA is fragmented to ~200 bp reads. Adaptors are added and one molecule is placed onto a bead.

The molecules are amplified on the bead by emulsion PCR. Each bead is placed into a single well of a slide. The slide is flooded with a single species of dNTP, along with buffers and polymerase, one dNTP at a time. The pH is detected in each of the wells, as each H+ ion released will decrease the pH. The changes in pH allow determination if that base, and how many thereof, was added to the sequence read. The dNTPs are washed away, and the process is repeated cycling through the different dNTP species. The pH change, if any, is used to determine how many bases (if any) were added with each cycle.

In ABI-SOLiD-based sequencing, a library of DNA fragments are prepared from the sample to be sequenced, and are used to prepare clonal bead populations where only one species of fragment will be present on the surface of each bead. The fragments attached to the beads will have a universal P1 adapter sequence attached so that the starting sequence of every fragment is both known and identical. Emulsion PCR takes place in microreactors. The resulting PCR products attached to the beads are then covalently bound to a glass slide. Primers hybridize to the P1 adapter sequence within the library template. A set of four fluorescently labelled di-base probes compete for ligation to the sequencing primer. Specificity of the di-base probe is achieved by interrogating every 1st and 2nd base in each ligation reaction. Multiple cycles of ligation, detection and cleavage are performed with the number of cycles determining the eventual read length. Following a series of ligation cycles, the extension product is removed and the template is reset with a primer complementary to the n−1 position for a second round of ligation cycles. Five rounds of primer reset are completed for each sequence tag. Through the primer reset process, each base is interrogated in two independent ligation reactions by two different primers. For example, the base at read position 5 is assayed by primer number 2 in ligation cycle 2 and by primer number 3 in ligation cycle 1.

In some cases, various next generation sequencing techniques are used to sequence a large number of nucleic acid fragments that were generated from long range PCRs. In some cases, nucleic acid from different individuals (e.g., two, three, four, five, six, seven, eight, nine, ten, eleven, twelve, or 20, 30, 40, 50, 60, 70, 80, 90, 100, 200, 500 or more, or any number therebetween, different humans) can be sequenced at the same time. In such cases, unique adaptors can be used for each individual such that each sequenced fragment can be assigned to the particular individual from which the fragment originated.

TaqMan® Assay

In one embodiment, the presence of rs144012689 can be detected using the TaqMan® assay. In this assay, one may utilize an oligonucleotide probe labeled with a reporter dye (e.g., fluorescent such as FAM or VIC) at the 5' end of the probe and a quencher dye (e.g., nonfluorescent quencher) at the 3' end of the probe. The proximity of the quencher to the intact probe maintains a low fluorescence for the reporter. During the PCR reaction, the 5' nuclease activity of DNA polymerase cleaves the probe, and separates the dye and quencher. Thus resulting in an increase in fluorescence of the reporter. Accumulation of PCR product is detected directly by monitoring the increase in fluorescence of the reporter dye. The 5' nuclease activity of DNA polymerase cleaves the probe between the reporter and the quencher only if the probe hybridizes to the target and is amplified during PCR. The probe is designed to straddle a target SNP position and hybridize to the nucleic acid molecule only if a particular SNP allele is present.

Genotyping is performed using oligonucleotide primers and probes. Oligonucleotides may be synthesized and prepared by any suitable methods (such as chemical synthesis), which are known in the art. Oligonucleotides may also be conveniently available through commercial sources. One of the skilled artisans would easily optimize and identify primers flanking the gene of interest in a PCR reaction. Commercially available primers may be used to amplify a particular gene of interest for a particular SNP. A number of computer programs (e.g., Primer-Express) is readily available to design optimal primer/probe sets. It will be apparent to one of skill in the art that the primers and probes based on the nucleic acid information provided (or publically available with accession numbers) can be prepared accordingly.

Methods for labeling of probes are known in the art. The labeled probes are used to hybridize within the amplified region during the amplification region. The probes are modified so as to avoid them from acting as primers for amplification. The detection probe is labeled with two dyes, one capable of quenching the fluorescence of the other dye when in proximity. One dye is attached to the 5' terminus of the probe and the other is attached to an internal site or the 3' terminus, so that quenching occurs when the probe is in a hybridized state.

Exemplary primers and probes are shown in Table 8 below. Two sets of primers are designed for nested PCR, with the first, outer set of primers ("pre-amp primer_forward" and "pre-amp primer_reverse") generating an about 120 bp amplicon, and the second, inner set ("primer_forward" and "primer_reverse") generating an about 70 bp amplicon. It should be noted that for regular Taqman assays, one primer set (e.g., the outer set) is sufficient. A nested PCR approach can be desirable to increase the TaqMan® assay signal intensity when, for example, small reaction volumn is used in a high-throughput screen and/or sample DNA content is low.

Two sets of three probes are also designed. The second bold and underlined letter in the probe sequences represents the location of rs144012689 (A/T); and the first bold and underlined letter represents another SNP (C/G) occurring within all the haplotypes targeted. Hence, three probes are included in the TaqMan® assay described herein, although typically two probes are sufficient in a regular TaqMan® assay targeting 1 SNP.

TABLE 8

Exemplary Sequences for TaqMan ® Assay Primers and Probes

| Primer sequences: | |
|---|---|
| pre-amp primer_forward | TCAAGCCCCAGGTAGAAGTGTT (SEQ ID NO: 1) |
| pre-amp primer_reverse | CATTGTCACATGTGCTGCACAA (SEQ ID NO: 2) |
| primer_forward | AGTGTTCCCT GCCTCATTAC (SEQ ID NO: 3) |
| primer_reverse | AGA GTA AGT GCT GGC ACA CA (SEQ ID NO: 4) |

| Probe sequences: | |
|---|---|
| FAM probe 1 | AAG CAG CAT CCT CAC AG (SEQ ID NO: 5) |
| VIC1 probe 1 | AAG CAG CAT CCA CAC AG (SEQ ID NO: 6) |
| VIC2 probe 1 | AAG CAG CAT GCA CAC AG (SEQ ID NO: 7) |
| FAM probe 2 | CAGCATCCTCACAGGGGCTAA (SEQ ID NO: 8) |

TABLE 8-continued

Exemplary Sequences for TaqMan ® Assay
Primers and Probes

| VIC1 probe 2 | CAGCATCCACACAGGGGCTAA<br>(SEQ ID NO: 9) |
| --- | --- |
| VIC2 probe 2 | CAGCATGCACACAGGGGCTAA<br>(SEQ ID NO: 10) |

The above exemplary primers and probes work well in practice in TaqMan® assays performed so far. However, one of ordinary skill in the art would appreciate that alternative primers and probes can be designed based on HLA-B gene sequence. Algorithms for designing primers and probes are widely used and readily available in the art (e.g., Primer-BLAST available at www.ncbi.nlm.nih.gov/tools/primer-blast/). In essence any primer(s) suitable for amplifying the HLA-B gene in a polymerase chain reaction can be used. In some embodiments it may be desirable to keep maximum amplicon size under 400 bp (e.g., 50-150 bp). The probe(s) should be designed to target the rs144012689 region, with suitable length (e.g., 18-22 bases but can be longer or shorter) and proper dye labeling as discussed herein.

In addition, one of ordinary skill in the art of design of primers will recognize that a given primer need not hybridize with 100% complementarity to prime the synthesis of a complementary nucleic acid strand. Primer pair sequences may be a "best fit" amongst several aligned sequences, thus they need not be fully complementary to the hybridization region of any one of the sequences in the alignment. Moreover, a primer may hybridize over one or more segments such that intervening or adjacent segments are not involved in the hybridization event (e.g., for example, a loop structure or a hairpin structure). The primers may comprise at least 70%, at least 75%, at least 80%, at least 85%, at least 90%, at least 95% or at least 99% sequence identity with a target nucleic acid of interest. Thus, in some embodiments, an extent of variation of 700 to 100%, or any range falling within, of the sequence identity is possible relative to the specific primer sequences disclosed herein.

To illustrate, determination of sequence identity is described in the following example. A primer 20 nucleobases in length which is identical to another 20 nucleobase primer having two non-identical residues has 18 of 20 identical residues (18/20=0.9 or 90% sequence identity). In another example, a primer 15 nucleobases in length having all residues identical to a 15 nucleobase segment of primer 20 nucleobases in length would have 15/20=0.75 or 75% sequence identity with the 20 nucleobase primer. Percent identity need not be a whole number, for example when a 28 consecutive nucleobase primer is completely identical to a 31 consecutive nucleobase primer (28/31=0.9032 or 90.3% identical). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some embodiments, complementarity of primers with respect to the conserved priming regions of target nucleic acid, is between about 70% and about 80%. In other embodiments, homology, sequence identity or complementarity, is between about 80% and about 90%. In yet other embodiments, homology, sequence identity or complementarity, is at least 90%, at least 92%, at least 94%, at least 95%, at least 96%, at least 97%, at least 98%, at least 99% or is 100%. In some embodiments, the primers used herein comprise at least 70%, at least 75%, at least 80%, at least 85%, at least 90%, at least 92%, at least 94;%, at least 95%, at least 96%, at least 98%, or at least 99%, or 100% (or any range falling within) sequence identity with the primer sequences specifically disclosed herein.

With primers and probes designed and synthesized, TaqMan® assay can be performed as follows. First, a 14-cycle pre-amplification (pre-amp) PCR is carried out with 125 ng genomic DNA per sample. Exemplary PCR program includes initial denaturation at 95° C. for 10 min, followed by 14 cycles of 15 sec denaturation at 95° C. and 4 min annealing and extension at 60° C., and hold at 4° C. for 1 hour and then 10° C. indefinitely. Then, the PCR product is diluted 1:5 (by adding 40 µl 1×TE into each 10 µl sample) and only 4.2 µl of the diluted PCR product is used for a total of 96 reactions. The sample master mix is prepared by mixing TaqMan® genotyping Master Mix, DNA polymerase, loading reagent and water. For each sample, 5.8 µl sample master mix and 4.2 µl diluted pre-amp PCR product is mixed. Then ~6 µl of mixture was loaded into the designated sample well. A 20× assay mix is prepared by mixing the primers and probes. For each assay, 100 µl 20× assay mix is mixed with 100 µl 2× assay loading reagent, and ~6 µl 10× assay mix is loaded into the designated assay well. A real-time PCR step is carried out after the sample and assay mix loading. Exemplary pre-amp PCR preparation, sample master mix and 20× assay mix preparation are shown in Table 9 below.

TABLE 9

Exemplary Assay Mix

| | Volume (µl) |
| --- | --- |
| Pre-amp PCR preparation: | |
| ABI PreAmp Master Mix 2X | 5 |
| Primer Pool (0.2X)* | 0.83 |
| 1XTE | 1.67 |
| DNA (50 ng/µl) | 2.5 |
| Total (for each sample) | 10 |
| Sample Master mix: | |
| Water | 0.2 |
| 20xGT sample loading reagent | 0.5 |
| ABI TaqMan ® genotyping Master Mix | 5 |
| AmpliTaq ® Gold DNA polymerase | 0.1 |
| Total (for each sample) | 5.8 |
| 20X Assay Mix preparation: | |
| primer_forward (100 µM) | 18.0 |
| primer_reverse (100 µM) | 18.0 |
| FAM probe (100 µM) | 12.0 |
| VIC1 probe (100 µM) | 3.0 |
| VIC2 probe (100 µM) | 3.0 |
| 1xTE | 46.0 |
| Total Volume | 100.0 |

*The pre-amp primer pool includes all the pre-amp primers for the 96 reactions. The concentration of the HLA primers is 1 µM each.

Real-time PCR can then be performed on any suitable real-time PCR machine such as those manufactured by Fluidigm or Applied Biosystems that can record fluorescence level in real-time.

Using this TaqMan® genotyping assay designed at the minor allele of rs144012689 to detect HLA-B*15:02, >1000 patient samples were tested in a high-throughput, cost-effective HLA-B*15:02 screening. The results are shown in Table 10 and FIG. 1, with a surprising 100/sensitivity and 100% specificity.

TABLE 10 rs144012689 minor allele detected by custom TaqMan ® real-time
PCR genotyping assay is correlated with HLA-B*15:02 status

| rs144012689 (minus strand, from HGX NGS sequencing) | HLA-B*15:02 (HGX NGS sequencing) | | Sensitivity | Specificity | PPV | NPV | P-value* |
|---|---|---|---|---|---|---|---|
| | + | − | | | | | |
| T/A (T is the minor allele) | TP (41) | FP (0) | 100% | 100% | 100% | 100% | <0.0001 |
| A/A (major allele) | FN (0) | TN (1040) | | | | | |

TP (true positive) = samples that were positive for both rs144012689 minor allele and HLA-B*15:02
FP (false positive) = samples that were positive for rs144012689 minor allele and were negative for HLA-B*15:02
FN (false negative) = samples that were negative for rs144012689 minor allele but were indeed positive for HLA-B*15:02
TN (true negative) = samples that were negative for rs144012689 minor allele and were also negative for HLA-B*15:02
PPV = positive predictive value;
NPV = negative predictive value;
*P value was calculated by two-tailed Fisher's exact-test.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments. Also, the phraseology and terminology used herein is for the purpose of description and should not be regarded as limiting.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for the use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items. "Consisting essentially of" means inclusion of the items listed thereafter and which is open to unlisted items that do not materially affect the basic and novel properties of the invention.

INCORPORATION BY REFERENCE

The ASCII text file submitted herewith via EFS-Web, entitled "010101USseq.txt" created on Jun. 28, 2016, having a size of 1,731 bytes, is incorporated herein by reference in its entirety.

All publications, patents and sequence database entries mentioned herein are hereby incorporated by reference in their entireties as if each individual publication or patent was specifically and individually indicated to be incorporated by reference.

The invention claimed is:

1. A non-naturally modified probe comprising a sequence selected from SEQ NO: 5, SEQ ID NO: 6, SEQ ID NO: 7, SEQ ID NO: 8, SEQ ID NO: 9 and/or SEQ ID NO: 10, wherein said probe has a detectable label attached thereto.

2. A double-stranded nucleic acid molecule comprising the non-naturally modified probe of claim 1 and a target sequence complementary and annealed to the probe, wherein said probe has a detectable label attached thereto.

3. A solid phase having a plurality of nucleic acids bound thereto, wherein the plurality of nucleic acids comprise one or more of the non-naturally modified probe of claim 1.

4. A solid phase having a plurality of nucleic acids bound thereto and a target sequence annealed to the nucleic acid, wherein the plurality of nucleic acids comprise one or more of the non-naturally modified probe of claim 1.

5. A kit for detecting the HLA-B*15:02 allele in a sample, comprising one or more of the non-naturally modified probes of claim 1.

6. The kit of claim 5, comprising three probes having the sequences of SEQ NO: 5, SEQ ID NO: 6, and SEQ ID NO: 7, respectively.

7. The kit of claim 5, comprising three probes having the sequences of SEQ ID NO: 8, SEQ ID NO: 9 and SEQ ID NO: 10, respectively.

8. The kit of claim 5, wherein the probe is labeled by a fluorescent dye at the 5' terminus and a quencher at the 3' terminus.

9. The kit of claim 5, further comprising:
a pair of primers designated at the HLA-B gene such that an amplicon produced therefrom includes rs144012689;
dNTPs; and
Taq DNA polymerase.

10. A method of treating a patient in need of carbamazepine, comprising:
obtaining a sample from the patient,
determining the presence or absence of rs144012689 minor allele T in the sample using one or more of the non-naturally modified probes of claim 1, and
in the absence of rs144012689 minor allele T, administering carbamazepine to the patient.

11. The method of claim 10, further comprising subjecting the sample to an assay selected from the group consisting of TaqMan® genotyping, SNP array and next generation sequencing.

12. The method of claim 11, wherein said TagMan® genotyping comprises subjecting the sample to a polymerase chain reaction in the presence of a TaqDNA polymerase, a pair of primers designated at the HLA-B gene such that an amplicon produced therefrom includes rs144012689, and a non-naturally modified probe that hybridizes with a portion of the amplicon at or near rs144012689.

13. The method of claim 12, further comprising subjecting the sample to TaqMan® genotyping with three probes having the sequences of SEQ ID NO: 5, SEQ ID NO: 6, and SEQ ID NO: 7.

14. The method of claim 12, further comprising subjecting the sample to TaqMan® genotyping with three probes having the sequences of SEQ ID NO: 8, SEQ NO: 9 and SEQ ID NO: 10.

15. The method of claim 12, wherein said probe has a reporter dye and a quencher dye attached thereto such that when both attached, the quencher dye quenches a signal from the reporter dye, and when one or both of the reporter dye and the quencher dye is released from the probe, the reporter dye emits the signal.

16. The method of claim 15, wherein the signal is fluorescence.

17. The method of claim 15, wherein one or both of the reporter dye and the quencher dye is capable of being released from the probe by Taq DNA polymerase when the probe is hybridized to the amplicon at or near rs144012689.

18. The method of claim 11, wherein said SNP array comprises a plurality of nucleic acids bound thereto, wherein the plurality of nucleic acids comprise one or more sequences selected from SEQ ID NO: 5, SEQ. ID NO: 6, SEQ ID NO: 7, SEQ ID NO: 8, SEQ ID NO: 9 and/or SEQ ID NO: 10.

19. The method of claim 18, further comprising hybridizing DNA from the sample to the plurality of nucleic acids.

20. The method of claim 19, further comprising labelling the DNA from the sample.

21. The method of claim 10, wherein the sample comprises genomic DNA.

* * * * *